United States Patent [19]

Holt

[11] 4,190,059
[45] Feb. 26, 1980

[54] APPARATUS FOR COLONIC LAVAGE AND SPECIMEN COLLECTION

[75] Inventor: Gregory G. Holt, Phoenix, Ariz.
[73] Assignee: Colonics Diversified, Inc., Scottsdale, Ariz.
[21] Appl. No.: 954,352
[22] Filed: Oct. 25, 1978
[51] Int. Cl.² .................... A61B 10/00; A61M 7/00
[52] U.S. Cl. ............................. 128/750; 128/229
[58] Field of Search ............... 128/227, 229, 66, 750, 128/760, 763, 766

[56] References Cited

U.S. PATENT DOCUMENTS

| | | | |
|---|---|---|---|
| 2,027,588 | 1/1936 | Hannon | 128/227 |
| 2,157,756 | 5/1939 | Irwin | 128/229 |
| 2,257,072 | 9/1941 | Coombs | 128/227 |
| 2,420,586 | 5/1947 | DeWelles | 128/227 |
| 2,522,122 | 9/1950 | Kertesz | 128/229 |
| 3,044,465 | 7/1962 | Anderson et al. | 128/229 |
| 3,771,522 | 11/1973 | Waysilk et al. | 128/227 |
| 3,823,714 | 7/1974 | Waysilk et al. | 128/229 |

*Primary Examiner*—Kyle L. Howell
*Attorney, Agent, or Firm*—Herbert E. Haynes, Jr.

[57] ABSTRACT

A unit including mechanisms and instrumentation for precision, temperature and pressure control of water which is directed through a speculum that continuously irrigates a patient's colon and drains the water along with extracted matter through an illuminated viewing chamber provided in the unit. The unit also includes an oxygen pressure regulator and a special mixing manifold by which the oxygen or other medicinal fluids may be optionally introduced into the water, and a device by which a specimen of extracted matter may be optionally retained for subsequent laboratory analysis.

22 Claims, 7 Drawing Figures

Fig. 2

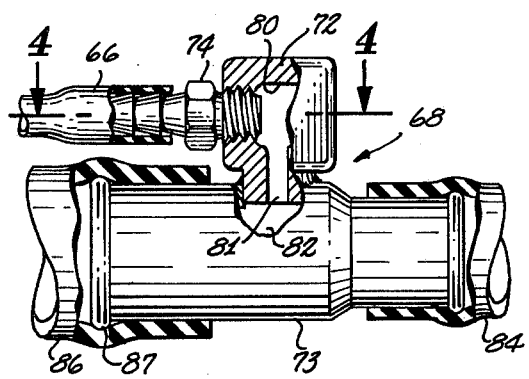
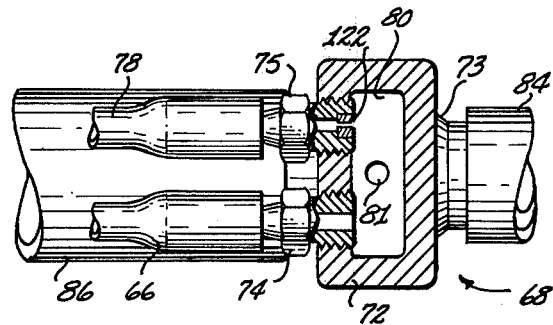
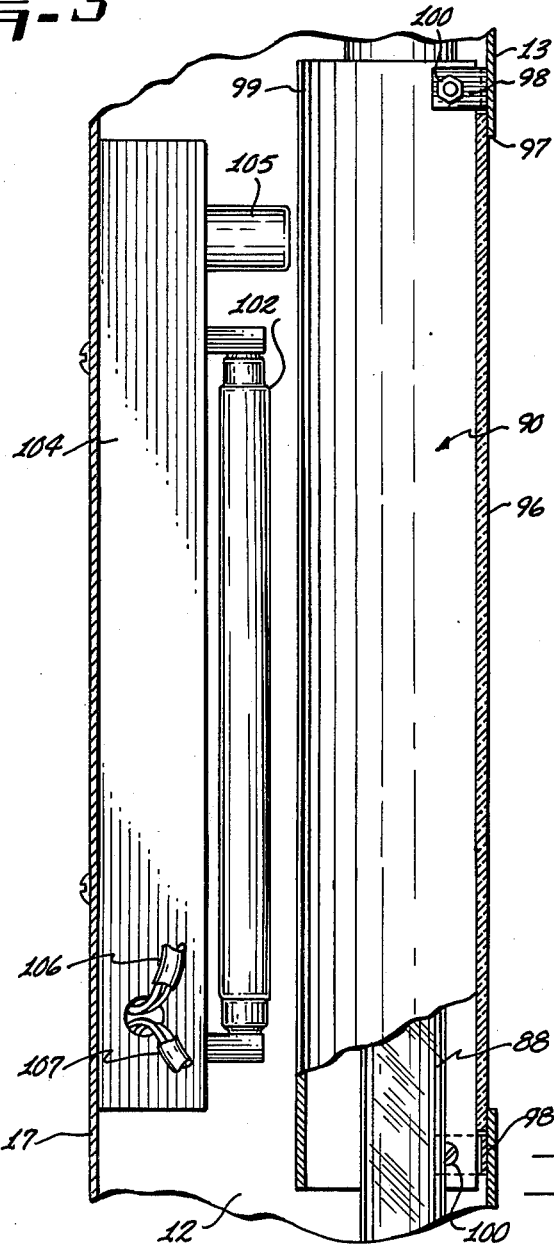

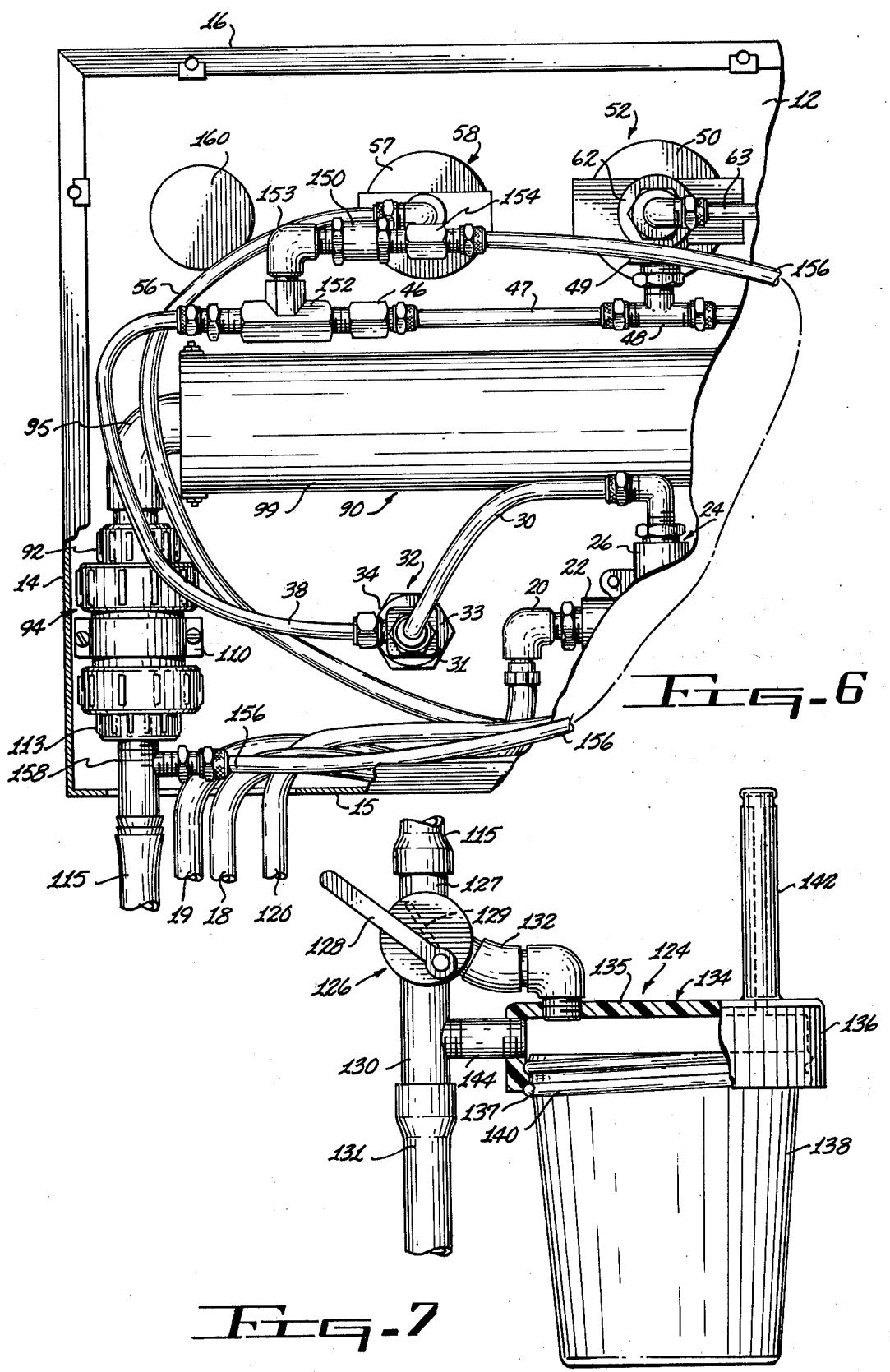

APPARATUS FOR COLONIC LAVAGE AND SPECIMEN COLLECTION

BACKGROUND OF THE INVENTION

1. Field of the Invention

This invention relates to medical equipment and more particularly to an apparatus for colonic lavage.

2. Description of the Prior Art

In the treatment of colitis and other ailments caused by impaction and/or infection of the colon, it has long been known that lavaging of the colon provides beneficial results, and that colonic lavaging mechanisms or systems must provide certain controls such as water temperature and pressure regulating devices, and others, to insure for the comfort and safety of a patient.

Examples of the prior art mechanisms and systems employed in colonic lavage may be seen in U.S. Pat. Nos. 2,157,756, 2,257,072, 2,420,586, 3,771,522 and 3,823,714. In general, these prior art mechanisms more or less provide the necessary control devices; however, the techniques employed and the design of the equipment itself has resulted in excessively bulky mechanisms which are difficult to set up, hard to use, cannot be considered as being truly portable, and are not precision devices as far as some of the control functions are concerned.

In most of the prior art mechanisms known to me, the lavaging mechanism is connected to a building's water supply plumbing system to obtain hot and cold water under pressure which is passed through a mixing valve to achieve water temperature control. The water is then delivered, by means of the water pressure, to an overhead tank or other reservoir means, and gravity is employed to detemine the pressure of the water delivered to a speculum. This design feature of the elevated reservoir, dictates that the prior art lavaging mechanisms be bulky in that a predetermined distance between the patient and the reservoir must be established. In some of the prior art systems, such as that fully disclosed in U.S. Pat. No. 3,771,522, the water reservoir is mounted on a wall approximately three and one-half feet above the patient, and the other control devices, such as the above mentioned water mixing valve, are also attached to the same wall for convenience reasons and to keep the system's plumbing lines to a reasonable length.

In other lavaging systems, such as that disclosed in U.S. Pat. No. 2,420,586, the above described elevated water reservoir and control devices are mounted within a cabinet, and the entire cabinet is hung on a wall or other vertical surface. It will be seen that in either of the above described typical systems, the lavaging mechanisms, in addition to being bulky, are not truly portable and cannot be readily set up for use and subsequently dismantled for storage until needed again. The need for mounting the prior art lavaging mechanisms on a wall at a specific height, for all intents and purposes, makes these mechanisms a more or less permanent installation, and due to the cost and short supply of medical space in general and treatment rooms in particular, the lack of portable and/or easily set up medical equipment is a decided disadvantage.

The elevated reservoir method of controlling water pressure to the speculum is, at best, a poor control device in that it is difficult if not impossible, to adjust the pressure to suit particular situations and patients. Raising and lowering of either the reservoir or the patient will, of course, change the water pressure, but this can only be described as a hit or miss type of control in that no degree of accuracy can be expected.

The above briefly described prior art lavaging systems will be seen to additionally include other controls such as: means for injecting oxygen into the water delivered to the speculum, means for injecting medicinal fluids into that same water, and some of the prior art units have provided viewing tubes by which the operator may visually inspect the matter extracted from the patient. Such a multiplicity of controls and other devices which normally include water flow controls and mixing valves, temperature gages, oxygen pressure regulators and switching devices, and the like, must be constantly monitored by the machine's operator, and this has not always been an easy job in that the controls, gages, etc. are scattered at various locations about the system or machanism.

To the best of my knowledge, no prior art lavaging mechanism has been devised which, in addition to patient considerations, has considered the operator with regard to ease of equipment set up and usage. Further, no prior art mechanism known to me has provided a means for easily collecting a sample or specimen of the matter extracted from a patient for subsequent laboratory analysis.

Therefore, a need exists for a new and improved colonic lavaging apparatus which overcomes some of the shortcomings and drawbacks of the prior art.

SUMMARY OF THE INVENTION

In accordance with the present invention, a new and improved apparatus for colonic lavage is disclosed as a portable unit with all the controls, gages, and other devices mounted in an easy to handle portable cabinet. The apparatus is adapted to be coupled to a building's water plumbing system to obtain hot and cold water under pressure. The water is directed through a mixing valve and a temperature gage to enable precision regulation of the water temperature. The water is also directed through a pressure regulating valve means which limits the maximum pressure of the water and provides for pressure adjustments below that maximum preset pressure limit. The water under precision pressure and temperature control is directed into a mixing manifold which is mounted upstream of a speculum. The water passing through the speculum will continuously irrigate a patient's colon to extract matter lodged therein. The extracted matter will flow with the irrigating water back through the speculum into an evacuation line which is coupled to an illuminated viewing chamber provided in the cabinet of the apparatus. After passing through the viewing chamber, the water and extracted matter will pass through a drain shutoff valve into a drain line, which extends from the cabinet to suitable disposal mechanisms, such as the toilet facilities of the building. The drain line contains a collection means by which a sample or specimen of the extracted matter may be optionally retained for subsequent transport to a laboratory for analysis.

In addition to the water and drain systems described above, the apparatus of the present invention is provided with a timing means for operator convenience, and an oxygen regulator and shutoff valve means, both of which are mounted on the face of the cabinet. Oxygen under pressure from an external source is coupled to the regulator and shutoff valve means which is connected to the mixing manifold mounted upstream of the speculum. In the water only operational mode, the mixing manifold simply passes the water to the speculum. In the water and oxygen operating mode, the water is aerated in the mixing manifold prior to entry into the speculum. The mixing manifold is also adapted so that the oxygen supply line may be disconnected therefrom and replaced by a fluid line which connects an external supply of suitable medicinal fluid to the manifold. In this latter operational mode, the mixing manifold mixes the medicinal fluid with the water prior to it being delivered to the speculum.

From the above, it will be seen that the water pressure regulation means of the apparatus of the present invention has eliminated the need for an elevated water reservoir, and in doing so has resulted in adjustable precision water pressure control, and has allowed the mechanism to be substantially reduced in size, has improved the ease of equipment set up and usage, and has provided convenient and simple means for collection of extracted matter specimens.

Accordingly, it is an object of the present invention to provide a new and improved apparatus for colonic lavage.

Another object of the present invention is to provide a new and improved apparatus for colonic lavage which is relatively easy to set up and use.

Another object of the present invention is to provide a new and improved apparatus for colonic lavage with the control devices and other operating mechanisms being contained in a relatively small easy to handle cabinet.

Another object of the present invention is to provide a new and improved apparatus for colonic lavage which includes means for precision control of water temperature and pressure.

Another object of the present invention is to provide a new and improved apparatus for colonic lavage in which water pressure control and adjustment is accomplished by a pressure regulating valve means that sets the maximum pressure of the water and provides means for adjustment of water pressure below the preset maximum pressure setting.

Another object of the present invention is to provide a new and improved apparatus of the above described character which provides means for precision regulation of oxygen under pressure for optional aeration of the water prior to its being supplied to a speculum.

Another object of the present invention is to provide an apparatus of the above type which includes a special mixing manifold upstream of the speculum by which the water delivered thereto may be optionally aerated by oxygen under regulated pressure, or may be mixed with a medicinal fluid prior to being passed into the speculum.

Still another object of the present invention is to provide a new and improved apparatus of the above described character which includes an illuminated viewing chamber mounted in the cabinet for visually inspecting the matter extracted from a patient.

Yet another object of the present invention is to provide a new and improved apparatus of the above type which further includes collection means in the drain line for optional retention of extracted matter specimens for subsequent laboratory analysis.

The foregoing and other objects of the present invention, as well as the invention itself, may be more fully understood from the following description when read in conjunction with the accompanying drawings.

BRIEF DESCRIPTION OF THE DRAWINGS

FIG. 2 is a rear elevational view of the apparatus of the present invention with portions of the cabinet removed and cut away to better illustrate the features thereof.

FIG. 3 is an enlarged fragmentary sectional view taken on the line 3—3 of FIG. 1.

FIG. 4 is a fragmentary sectional view taken on the line 4—4 of FIG. 3.

FIG. 5 is an enlarged fragmentary sectional view taken along the line 5—5 of FIG. 1, and having portions thereof broken away to illustrate the various features.

FIG. 6 is a fragmentary rear elevational view similar to FIG. 2 and illustrating a modification of the apparatus of the present invention.

FIG. 7 is an elevational view of the collection means device of the present invention with portions of the collection means being broken away to illustrate the various feaures thereof.

DESCRIPTION OF THE PREFERRED EMBODIMENTS

Figure 1:
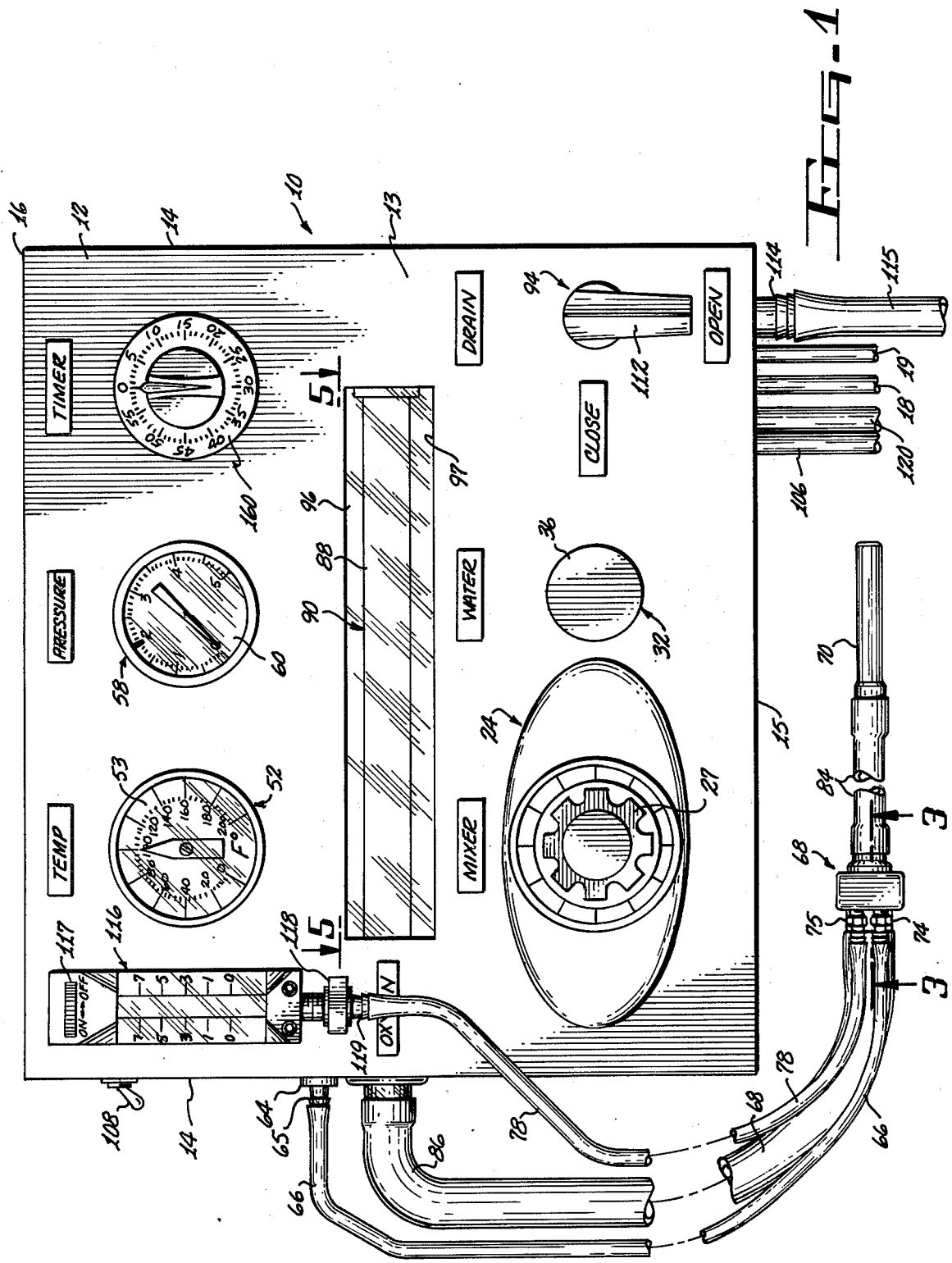
FIG. 1 is a front elevational view of the colonic lavage apparatus of the present invention illustrating the various features thereof.
Figure 2:
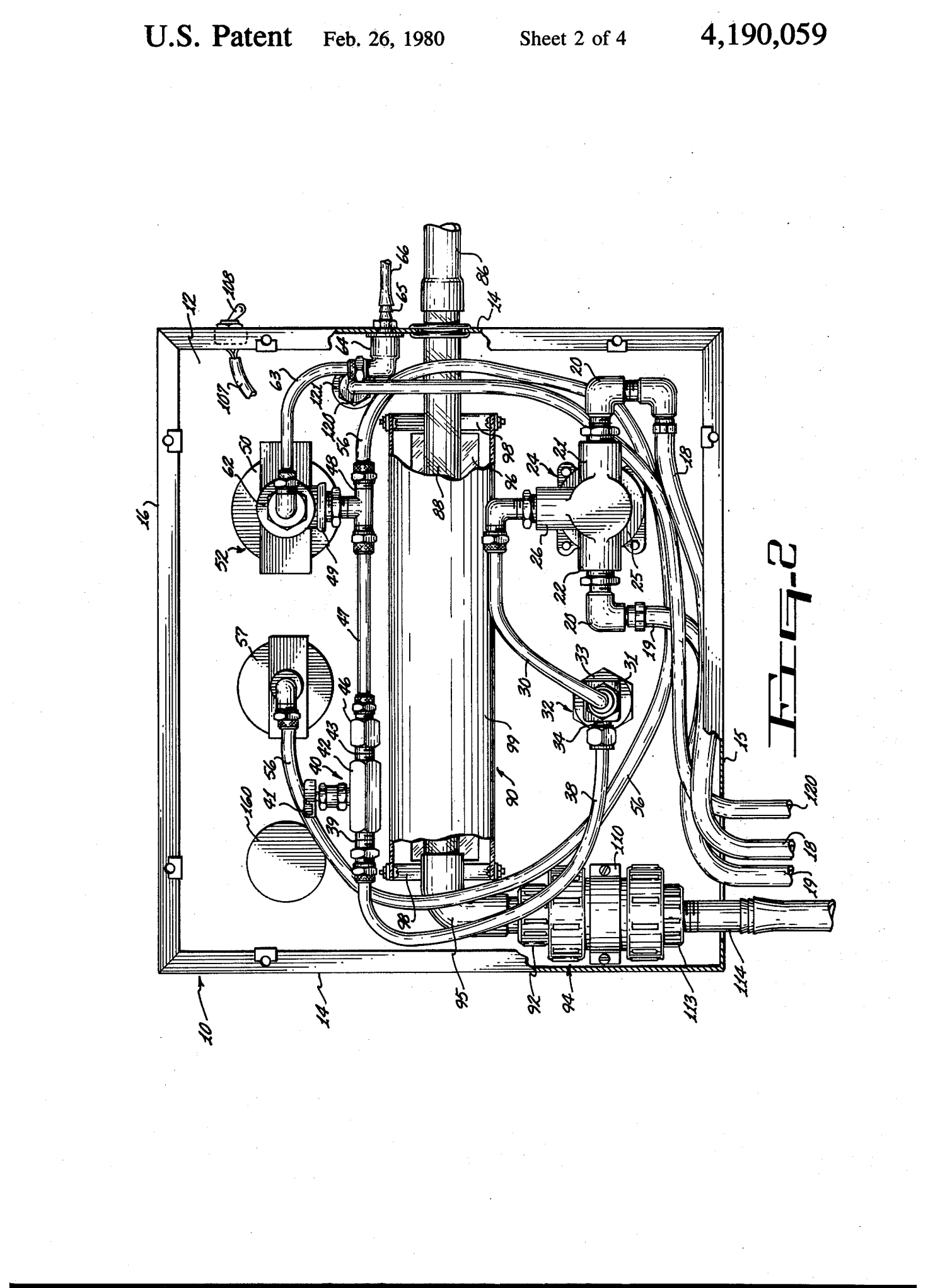

Referring more particularly to the drawings, FIGS. 1 and 2 show the colonic lavage apparatus of the present invention which is indicated generally by the reference numeral 10.

The apparatus 10 includes a housing or cabinet 12 having a front panel 13, opposed side walls 14, bottom wall 15, top wall 16, and a demountable back panel 17 (FIG. 5) which has been omitted from FIG. 2 for clarity.

The bottom wall 15 of the cabinet 12 has an enlarged opening formed therein through which, among other things, a hot water hose 18 and a cold water hose 19 pass into the interior of the cabinet. The water hoses 18 and 19 are coupled by means of suitable fittings 20 to the hot water inlet port 21 and the cold water inlet port 22, respectively, of a water mixing valve 24 mounted on the front panel 13 of the cabinet. The opposite ends (not shown) of the hot and cold water hoses, 18 and 19, are suitably adapted for connection to suitable sources of hot and cold water under pressure, such as conventional faucets (not shown) of a building's water supply plumbing system.

The water mixing valve 24 is provided with a housing 25 which protrudes from the rear surface of the front panel 13 into the interior of the cabinet 12, and in addition to the previously mentioned hot and cold water inlet ports 21 and 22, has a mixed water outlet port 26 formed thereon. The mixer valve 24 extends through the front panel 13 in the normal manner and has a rotatable temperature adjusting knob 27 (FIG. 1) mounted thereon. The water mixing valve 24 operates in a well known manner to modulate the incoming hot and cold water under pressure to arrive at a desired temperature with the mixed water emerging from the outlet port 26. Many mixing valves of this basis type are commercially available, however, due to the nature of the apparatus 10, it is preferred that a mixing valve of high quality and precision be used, with one such valve being identified as: POWERS HYDROGUARD, Series 420, available from the Powers-Flat Division of the Powers Regulator Company of Skokie, Ill., 60076.

Water emerging from the outlet port 26 of the mixing valve 24 is supplied, by means of a suitable hose 30, to the inlet port 31 of a conventional water pressure control valve 32. The control valve 32 has a housing 33 which, in addition to the inlet port 31, has an outlet port 34, with the housing and its ports being located in the interior of the cabinet 12. The valve 32 is mounted in the front panel 13 of the cabinet in the usual manner, and is provided with a rotatable pressure regulating control knob 36 (FIG. 1).

A hose 38 is suitably coupled to the outlet port 34 of the pressure control valve 32 for transporting the water emerging therefrom to the inlet port 39 of a water pressure limiting valve 40. The pressure limiting valve 40 is a conventional type of device which adjustably restricts the flow rate of the water passing therethrough, with the adjustment being accomplished by means of a rotatable handle 41 suitably provided on the valve housing 42. It will be noted that the pressure limiting valve 40 is not mounted in the front panel 13 of the cabinet 12, but is instead entirely contained within the interior thereof. The valve 40 may be suitably supported in the cabinet by connection (not shown) to any appropriate surface or protruding element, or may be positioned between the hoses coupled thereto as shown. In any event, the pressure limiting valve 40 is contained entirely within the cabinet 12 to prevent unauthorized adjustments or other tampering. It will be understood that although the pressure limiting valve 40 is shown and described as being manually adjustable, it may take the form of a fixed valve (not shown) such as one that is fixedly set at the factory.

The water pressure control valve 32 and the water pressure limiting valve 40 cooperate to form a water pressure regulating valve means which is employed in the apparatus 10 of the present invention to limit the maximum pressure of the water, and to provide pressure adjustment means below that maximum preset pressure limit. In operation, the pressure limiting valve 40 is preset so that the water exiting from the outlet port 43 thereof will not exceed a pressure of approximately 3 psi. Thus, the pressure control valve 32 is employed to vary the water pressure in the range of from 0—3 psi.

The pressure and temperature regulated water emerging from the outlet port 43 of the pressure limiting valve 40 passes through a check valve 46 which is a conventional well known type of device such as a ball check valve which allows water to flow from the limiting valve 40 and will stop reverse flow thereof.

A hose 47 is suitably coupled to the outlet end of the check valve 46 to convey the water to a tee 48, one branch of which is threadingly connected to an inlet boss 49 provided on the housing body 50 of a temperature gage 52. The temperature gage 52 is suitably mounted in the front panel 13 of the cabinet 12 so that the housing body protrudes into the interior of the cabinet, and a dial face 53 (FIG. 1) is exposed for convenient viewing on the exterior surface of the front panel. It will now be seen that the water mixing valve 24 and the temperature gage 52 cooperate to provide means for precision temperature control of the water with that gage and valve being conveniently arranged to facilitate operation of the apparatus 10.

As previously mentioned, one outlet branch of the tee 48 is mounted in the inlet boss 49 of the temperature gage 52. The other branch of that same tee 48 has a hose 56 connected thereto, with the hose looping downwardly toward the bottom of the cabinet 12, and back up for connection to the housing body 57 of a pressure gage 58. As was the case with regard to the temperature gage 52, the pressure gage 58 is similarly mounted in the front panel 13 of the cabinet 12 so that its body 57 protrudes into the interior of the cabinet 12 and its dial face 60 (FIG. 1) is disposed for viewing on the exterior surface of the front panel. The looped positioning of the hose 56 is a well known technique for providing an air buffer in the hose proximate the pressure gage 58 so that the pressure of the water being sensed will be transferred to the air buffer and thus water will not enter into the internal workings of the gage. The pressure gate 58, in conjunction with the previously described water pressure regulating valve means provides the apparatus 10 with means for precision control of the water pressure.

The water, which is regulated as to its pressure and temperature as hereinbefore described, will exit a water outlet boss 62 provided on the housing body 50 of the temperature gage 52 and will pass through a hose 63 which has one of its ends connected to the boss and has its other end connected to an elbow 64 mounted in one of the side walls 14 of the cabinet 12. The elbow 64 is provided with a hose barb 65 which passes through the side wall 14 and has one end of a water supply hose 66 mounted thereon.

As shown in FIG. 1, the water supply hose 66 extends from the cabinet 12 and has its other end connected to a mixing manifold 68 which, as hereinafter will be described in detail, is coupled to a speculum 70.

The mixing manifold 68, as seen best in FIGS. 3 and 4, is of special configuration which includes a mixer housing 72 mounted on the periphery of a tubular body 73. The mixer housing 72 has a spaced pair of fittings 74 and 75 threadingly carried in suitable threaded bores formed therein. Both of the fittings 74 and 75 have extending barbed ends with the end of the fitting 74 providing a first inlet port to which the water supply hose 66 is mounted. The other fitting 75 provides a second inlet port through which an auxiliary medicinal fluid may be optionally admitted to the mixer housing and is shown in the preferred embodiment as having one end of an oxygen hose 78 mounted thereon as will hereinafter be described. Both of the fittings communicate with an interior cavity 80 provided within the mixer housing 72. A passage 81 extends between the cavity 80 of the housing 72 and the bore 82 of the tubular body 73 so that the temperature and pressure regulated water delivered by the supply hose 66 will pass through the fitting 74, into the cavity 80, through the passage 81 and into the bore 82 of the tubular body 73.

One of the ends of the tubular body 73 of the mixing manifold 68 has a hose 84 coupled thereto with that hose being connected to the speculum 70. As is well known in the art, a speculum is a device for insertion into the anal canal of a patient, thus the water exiting from the mixing manifold 68 will pass through the hose 84, the speculum 70, into the colon of a patient where it will loosen matted lodged therein by an irrigation process. When the colon becomes full of water, a reverse flow will commence so that the water and extracted matter will flow back through the speculum 70, through the hose 84, through the tubular body 73 of the mixing manifold 68 and into a hose 86 which is connected to a discharge port 87 provided on the tubular body 73.

The hose 86 extends from the discharge port 87 of the tubular body 73 of the mixing manifold 68 to the inlet end of a transparent sight tube 88 which is mounted in the cabinet 12 so that the inlet end extends through the side wall 14 of the cabinet. The transparent sight tube passed through an illuminated viewing chamber 70 which is provided in the cabinet 12, and has its outlet end connected to the inlet boss 92 of a drain shutoff valve 94 by means of a suitable elbow 95.

The illuminated viewing chamber 90 as best seen in FIGS. 2 and 5, includes a sheet 96 of transparent material affixed, such as by a suitable adhesive (not shown), so as to span an opening 97 formed through the front panel 13 of the cabinet 12. A pair of substantially U-shaped brackets 98 are mounted on the interior surface of the front panel 13 so that each of those brackets is disposed adjacent a different side end of the opening 97. An elongated translucent panel 99 which is arcuate in cross section, is positioned behind the transparent sheet 96 and is held in that position by having its opposite ends attached to the brackets 98 such as with the screws 100. A fluorescent light 102 is mounted in the nornal manner on a bracket 104 which is affixed to the demountable rear panel 17 of the cabinet 12. The bracket 104 is positioned so that the fluorescent light 102 is disposed immediately behind the translucent panel 99 and is coextensive therewith. The bracket 104 also provides means for mounting the ballast unit 105, and containing the usual wiring. The wiring includes a power cord 106 which is adapted to extend from the bracket 104 and exit the cabinet 12 through the enlarged opening formed in the bottom panel 15 of the cabinet 12, as shown in FIG. 1. The power cord 106 is adapted to be plugged into any conventional electrical outlet, and another line 107 is connected to an on-off switch 108 (FIG. 2) mounted in the side wall 14 of the cabinet 12.

The above described illuminated viewing chamber 90, having the sight tube 88 passing through the space between the transparent sheet 96 and the translucent arcuate panel 99, is provided in the apparatus 10 so that during colonic irrigation, the extracted matter may be visually inspected by the operator of the apparatus.

The drain shutoff valve 94 is mounted to the front panel 13 of the cabinet 12 by a suitable bracket 10, so as to be disposed immediately above the enlarged opening formed in the bottom wall 15 of the cabinet 12. The drain shutoff valve 94 is a conventional well known type of device, which, as seen in FIG. 1, is provided with a lever 112 which is manually movable between an open and a closed position. The outlet boss 113 of the drain valve 94 has a barbed nipple 114 mounted therein, upon which a drain hose 115 is mounted.

A drain shutoff valve suitable for this installation may be purchased from CELANESE PIPING SYSTEMS, INC., of 2929 W. Magazine Street., Louisville, Ky.- 40211, and is identified as Part No. 21599008.

As seen in FIG. 1, an oxygen pressure regulator and shutoff valve 116 is suitably mounted on the exterior surface of the front panel 13 of the cabinet 12. The oxygen valve 116 includes a shutoff knob 117 at its upper end, and has a pressure regulating knob 118 mounted on its lower end. The lower end of the valve 116 is the oxygen outlet, and is provided with a barbed nipple 119 on which the hereinbefore mentioned oxygen hose 78 is mounted. Oxygen under pressure from a remote external source (not shown) is supplied by a suitable hose 120, as best seen in FIG. 2, to an inlet port 121 which extends rearwardly from the valve 116 through the front panel 13 into the interior of the cabinet 12. The oxygen hose 78 mounted on the outlet nipple 119 of the valve 116 is connected to the fitting 75 of the mixer manifold 68, as hereinbefore described, to deliver oxygen under pressure to the cavity 80 of the manifold. As seen in FIG. 4 the fitting 75 is provided with an orifice 122 therein so that the oxygen will be delivered into the cavity at a high velocity so that it will aerate the water that is supplied to the cavity 80 through the fitting 74.

Any of several high qaulity oxygen regulator and shutoff valves may be employed in the apparatus 10 of the present invention, such as the one identified as the PURITAN FLO-METER NO. 124,108 available from the PURITAN-BENNET CO., Kansas City, Mo.- 64106.

The above described barbed ends of the fittings 74 and 75 provide a low cost method of commecting the hoses 66 and 78 to the mixer manifold 68, and such a method will suffice in most instances, however, in some situations it may be desirable to provide at least the fitting 75 with a suitable quick disconnect type of coupling device (not shown). The advantage of such a quick disconnect fitting (not shown) will be appreciated upon consideration of the desirability in some instances, of supplying an auxiliary medicinal fluid (not shown) to the manifold 68 instead of oxygen. In such situations, the oxygen hose 78 is decoupled from the fitting 75, or a quick disconnect equivalent thereof, and is replaced by a medicinal fluid hose (not shown) which supplies such a fluid from an external source (not shown) to the cavity 80 of the mixer manifold 68, where it is mixed with the water prior to delivery to the speculum 70. Examples of an auxiliary medicinal fluid may be air under pressure, medicinal liquid and the like.

Reference is now made to FIG. 7 wherein a specimen collection means is shown and which is identified in its entirety by the reference numeral 124. The specimen collection means 124 includes a manually operable flow diverting valve 126 having its inlet end 127 suitably coupled to the drain hose 115 that extends from the bottom of the cabinet 12. The flow diverting valve 126 is shown as a conventional flapper type of valve which employs a manually operable lever 128 to appropriately position a flapper 129. In the normal position (not shown) of the flapper 129, the water and extracted matter will flow straight through the flow diverting valve 126 so that it will exit from the outlet end 130 of the valve and will be transported to a suitable disposal facility (not shown) by a dump line 131 that is mounted on the outlet end 130. In the flow diverting position of the flapper 129, as shown in FIG. 7, the water and extracted matter is directed by the flapper to a diversion branch 132 of the valve 126, with the diversion branch having its outlet end threadingly attached to the top of a cover shaped body or housing 134. The cover shaped body 134 has a planar top 135 with an integral depending endless side wall 136 with internal threads 137 formed therein so that the threads circumscribe a downwardly opening bore formed in the cover body. A suitable container 138 having an externally threaded rim 140 is threadingly mounted in the downwardly opening bore of the cover body 134 for collecting and retaining specimens of the matter extracted from a patient, as will become apparent as this description progresses. The cover body 134 is provided with an air vent standpipe 142 to allow air to escape as the container 138 is being filled, and is provided with an overflow pipe 144 which extends laterally from the side wall 136, and is connected to the flow diverting valve 126 immediately upstream of the outlet end 130 thereof.

In operation, the operator of the apparatus 10 upon visually detecting something in the sight tube 88 which he considers as warranting further attention, can collect a specimen of that extracted matter by manually operating the flow diverting valve 126 so that the extracted matter and water will flow through the diversion branch 132 into the container 138. Since the extracted matter is, for the most part, heavier than the water, it will settle in the container and some of the water will exit therefrom through the overflow pipe 144. When the container 138 is full, or when a sufficient amount of the extracted matter has been collected, the operator returns the flow diverting valve 126 to its normal or first position, removes the container 138 and replaces it with another. The container is then closed with a suitable cover (not shown) and is subsequently taken to a laboratory for analysis.

Reference is now made to FIG. 6 wherein a modification of the apparatus 10 of the present invention is shown. In this embodiment, the water pressure control function of the apparatus is accomplished by employing the water pressure control valve 32 in the manner hereinbefore described, and the pressure limiting operation is accomplished by a pressure relief valve 150. The water exiting from the pressure control valve 32 through the hose 38 is directed to the inlet port of a tee 152 which has one of its outlet ports connected by means of an elbow 153 to the inlet of the pressure relief valve 150. The outlet of the pressure relief valve 150 is connected to a bypass means in the form of a suitable check valve 154 which allows water to flow from the pressure relief valve and prevents reverse flow thereof, with the outlet end of the check valve 154 having one end of a hose 156 connected thereto with the other end of that same hose being connected to a special tee 158 threadingly mounted in the outlet boss 113 of the drain shutoff valve 94. The other outlet port of the tee 152 is connected to the check valve 46 which in turn is connected to the hose 47 which leads to the tee 48 mounted in the temperature gage 52 as previously described with reference to the embodiment shown in FIG. 2.

The pressure relief valve 150 is a well known type of device which will remain closed when the water pressure is below a predetermined value. That value, which as hereinbefore suggested, is approximately 3 psi, is built into the relief valve 150 at the factory. When the water pressure at the inlet to the pressure relief valve 150 exceeds the predetermined value, the relief valve 150 will open so as to bypass some of the water into the drain hose 115. The amount that the pressure relief valve 150 opens is determined by the water pressure at its inlet end, i.e., when the water pressure increases, the valve 150 will open more to bypass a larger amount of the water into the drain hose 115. In this manner, the pressure of the water in the tee 152, and thus, throughout the apparatus 10 will be limited to the value at which the pressure relief valve will open.

In view of the above, it will now be seen that the apparatus 10 of the present invention is provided with the pressure regulating valve means which may include the first described embodiment of the pressure control valve 32 in combination with the pressure limiting valve 40, or the latter described embodiment which comprises the pressure control valve 32 in combination with the pressure relief valve 150.

Although not entering directly into the colonic lavage function of the apparatus 10, for operator convenience, the apparatus is provided with a suitable timing device 160 which is carried in the front panel 13 of the cabinet. The timing device 160 is used by the operator to time the duration that a patient is to be given a colonic lavage.

While the principles of the invention have now been made clear in an illustrated embodiment, there will be immediately obvious to those skilled in the art, many modifications of structure, arrangements proportions, the elements, materials, and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claim is:

1. An apparatus for colonic lavage comprising:
   (a) a water mixing valve for receiving hot and cold water under pressure and mixing them to arrive at a desired temperature, said mixing valve having an outlet port;
   (b) water pressure regulating valve means coupled to the outlet port of said water mixing valve for receiving water therefrom, said water pressure regulating valve means having an outlet and including first valve means for limiting the maximum pressure of the water at its outlet and second valve means for adjusting the water pressure to specific valves below that maximum limit;
   (c) a water temperature gage coupled to the outlet of said water pressure regulating valve means to provide a visual indication of the water temperature;
   (d) a water pressure gage coupled to the outlet of said water pressure regulating valve means to provide a visual indication of the water pressure at the outlet of said water pressure regulating valve means;
   (e) a speculum for insertion into the anal canal of a patient for lavaging the patient's colon and extracting matter lodged therein; and
   (f) manifold means connected between the outlet of said water pressure regulating valve means and said speculum for delivering water to said speculum and for receiving the extracted matter therefrom, said manifold means having a discharge port through which the extracted matter passes.

2. An apparatus as claimed in claim 1 wherein said water pressure regulating valve means comprises:
   (a) said first valve means for limiting the maximum pressure of the water is a flow limiting valve set to allow a maximum flow of water therethrough, said flow limiting valve having an inlet port and an outlet port with that outlet port being the outlet of said water pressure regulating valve means; and
   (b) said second valve means for adjusting the water pressure to specific valves below the maximum limit is an adjustable flow control valve having an inlet port which is connected to the outlet port of said water mixing valve and having an outlet port which is connected to the inlet port of said flow limiting valve.

3. An apparatus as claimed in claim 1 wherein said water pressure regulating valve means comprises:
   (a) said first valve means for limiting the maximum pressure of the water is a pressure relief valve set to open when the water pressure exceeds a predetermined value, said pressure relief valve having an inlet port and an outlet port;

(b) a tee having an inlet port and a pair of outlet ports one of which is connected to the inlet port of said pressure relief valve and the other of which is the outlet of said water pressure regulating valve means;

(c) said second valve means for adjusting the water pressure to specific values below the maximum limit is an adjustable flow control valve having an inlet port which is coupled to the outlet port of said water mixing valve and having an outlet port which is coupled to the inlet port of said tee; and (d) bypass means connected to the outlet port of said pressure relief valve for receiving the water which passes therethrough when said pressure relief valve is open.

4. An apparatus as claimed in claim 1 wherein said manifold means comprises:

(a) a mixing housing having an internal cavity, said mixing housing having a first inlet port which is coupled to the outlet of said water pressure regulating valve means for receiving water therefrom and directing that water into the internal cavity; and (b) a tubular housing attached to said mixing housing with a passage communicating between the internal cavity of said mixing housing and the bore of said tubular housing, one end of said tubular housing being a port which is coupled to said speculum and the other end being the discharge port through which the extracted matter received from said speculum passes.

5. An apparatus as claimed in claim 4 wherein said mixing housing is further provided with a second inlet port for admitting an auxiliary fluid medium to the internal cavity of said mixing housing when an auxiliary fluid medium is supplied to said second inlet port.

6. An apparatus as claimed in claim 5 and further comprising an oxygen pressure regulator and shutoff valve having an inlet port for receiving oxygen under pressure from an external source, said oxygen pressure regulator and shutoff valve having an outlet port and adapted for optionally delivering oxygen at a regulated pressure to that outlet port, the outlet port of said oxygen pressure regulator and shutoff valve being connectable to the second inlet port of said mixing housing.

7. An apparatus as claimed in claim 1 and further comprising:

(a) a cabinet having a front panel in which an opening is formed;

(b) a viewing chamber mounted in said cabinet immediately behind the opening formed in the front panel thereof;

(c) means in said cabinet for illuminating said viewing chamber; and (d) a transparent sight tube mounted in said cabinet so as to pass through said viewing chamber, said transparent sight tube having an inlet end which is coupled to the discharge port of said manifold means for receiving the extracted matter therefrom.

8. An apparatus as claimed in claim 1 and further comprising a drain shutoff valve having an inlet end which is coupled to the discharge port of said manifold means for receiving the extracted matter therefrom.

9. An apparatus as claimed in claim 1 and further comprising a specimen collection means coupled to the discharge port of said manifold means for optionally collecting a specimen of the extracted matter.

10. An apparatus as claimed in claim 1 and further comprising:

(a) a cabinet having a front panel in which an opening is formed;

(b) a viewing chamber mounted in said cabinet immediately behind the opening formed in the front panel thereof;

(c) means in said cabinet for illuminating said viewing chamber;

(d) a transparent sight tube mounted in said cabinet so as to pass through said viewing chamber, said transparent sight tube having an inlet end and an outlet end with that inlet end coupled to the discharge port of said manifold means for receiving the extracted matter therefrom;

(e) a drain shutoff valve having an inlet port and an outlet port with that inlet port being coupled to the outlet end of said transparent sight tube for receiving the extracted matter therefrom; and (f) a specimen collection means coupled to the outlet port of said drain shutoff valve, said specimen collection means being operable to optionally collect a specimen of the extracted matter received from said drain shutoff valve.

11. An apparatus for colonic lavage comprising:

(a) a cabinet having a front panel;

(b) a water mixing valve for receiving hot and cold water under pressure and mixing them to arrive at a desired temperature, said mixing valve mounted in the front panel and having an outlet port;

(c) water pressure regulating valve means coupled to the outlet port of said water mixing valve for receiving water therefrom, said water pressure regulating valve means having an outlet and including first valve means contained within said cabinet for limiting the maximum pressure of the water and a second valve means mounted in the front panel of said cabinet for adjusting the water pressure at various valves below that maximum limit;

(d) a water temperature gage coupled to the outlet of said water pressure regulating valve means to provide a visual indication of the water temperature, said water temperature gage mounted in the front panel of said cabinet;

(e) a water pressure gage coupled to the outlet of said water pressure regulating valve means to provide a visual indication of the water pressure at the outlet of said water pressure regulating valve means, said water pressure gage mounted in the front panel of said cabinet;

(f) a speculum for insertion into the anal canal of a patient for lavaging that patient's colon and extracting matter lodged therein; and (g) manifold means connected between the outlet of said water pressure regulating valve means and said speculum for delivering water to said speculum and for receiving the extracted matter therefrom, said manifold means having a discharge port through which the extracted matter passes.

12. An apparatus as claimed in claim 11 wherein said water pressure regulating valve means comprises:

(a) said first valve means for limiting the maximum pressure of the water is a flow limiting valve set to allow a maximum rate of water flow therethrough, said flow limiting valve having an inlet port and an outlet port with that outlet port being the outlet of said water pressure regulating valve means; and (b) said second valve means for adjusting the water pressure to various values is an adjustable flow control valve having an inlet port which is connected to the outlet port of said water mixing valve and having an outlet port which is connected to the inlet port of said flow limiting valve.

13. An apparatus as claimed in claim 11 wherein said water pressure regulating valve means comprises:
(a) said first valve means for limiting the maximum pressure of the water is a pressure relief valve set to open when the water pressure exceeds a predetermined value, said pressure relief valve having an inlet port and an outlet port;
(b) a tee having an inlet port and a pair of outlet ports one of which is connected to the inlet port of said pressure relief valve and the other being the outlet of said water pressure regulating valve means;
(c) said second valve means for adjusting the water pressure at various values is an adjustable flow control valve having an inlet port which is coupled to the outlet port of said water mixing valve and having an outlet port which is coupled to the inlet port of said tee; and
(d) bypass means connected to the outlet port of said pressure relief valve for receiving the water which passes therethrough when said pressure relief valve is open.

14. An apparatus as claimed in claim 11 wherein said manifold means comprises:
(a) a mixing housing having an internal cavity and a first inlet port which is coupled to the outlet of said water pressure regulating valve means for receiving water therefrom and directing it into the internal cavity; and
(b) a tubular housing attached to said mixing housing with a passage communicating between the internal cavity of said mixing housing and the bore of said tubular housing, one end of said tubular housing being a port which is coupled to said speculum and the other end is the discharge port.

15. An apparatus as claimed in claim 14 wherein said mixing housing is further provided with a second inlet port for admitting an auxiliary fluid medium to the internal cavity of said mixing housing when an auxiliary fluid medium is supplied to the second inlet port.

16. An apparatus as claimed in claim 15 and further comprising an oxygen pressure regulator and shutoff valve mounted on the front panel of said cabinet, said oxygen pressure regulator and shutoff valve having an inlet port for receiving oxygen under pressure from a remote source and having an outlet port, said oxygen pressure regulator and shutoff valve adapted for optionally delivering oxygen at a regulated pressure to the outlet port thereof with that outlet port being connectable to the second inlet port of said mixing housing.

17. An apparatus as claimed in claim 11 and further comprising:
(a) said front panel of said cabinet having an opening formed therethrough;
(b) a viewing chamber in said cabinet immediately behind the opening formed in the front panel thereof;
(c) means in said cabinet for illuminating said viewing chamber; and
(d) a transparent sight tube mounted in said cabinet so as to pass through said viewing chamber, said transparent sight tube having an inlet end and an outlet end with that inlet end being coupled to the discharge port of said manifold means for receiving the extracted matter therefrom.

18. An apparatus as claimed in claim 11 and further comprising a drain shutoff valve mounted in said cabinet and having an inlet port and an outlet port with that inlet port being coupled to the discharge port of said manifold means.

19. An apparatus as claimed in claim 11 and further comprising a specimen collection means coupled to the discharge port of said manifold means for optional collection of a specimen of the extracted matter.

20. An apparatus as claimed in claim 11 and further comprising:
(a) said cabinet having an opening formed through the front panel thereof;
(b) a viewing chamber in said cabinet immediately behind the opening formed through the front panel thereof;
(c) means in said cabinet for illuminating said viewing chamber;
(d) a transparent sight tube mounted in said cabinet and disposed to pass through said viewing chamber, said transparent sight tube having an inlet end and an outlet end with that inlet end being coupled to the discharge port of said manifold means for receiving the extracted matter therefrom;
(e) a drain shutoff valve mounted in said cabinet and having an inlet port and an outlet port with that inlet port being coupled to the outlet end of said transparent sight tube for receiving the extracted matter therefrom; and
(f) a specimen collection means coupled to the outlet port of said drain shutoff valve, said specimen collection means being operable for optional collection of a specimen of the extracted matter received from said drain shutoff valve.

21. An apparatus as claimed in claim 20 wherein said viewing chamber comprises:
(a) a transparent sheet affixed to the front panel of said cabinet to cover the opening formed therethrough;
(b) a translucent panel of arcuate cross section within said cabinet adjacent said transparent sheet; and
(c) bracket means for mounting said translucent panel to the inwardly facing surface of the front panel of said cabinet.

22. An apparatus as claimed in claim 20 wherein said specimen collection means comprises:
(a) a flow diverting valve having an inlet end connected to the outlet port of said drain shutoff valve for receiving the extracted matter therefrom and having an outlet end and a diversion branch, said flow diverting valve being manually operable from a first position which places the inlet end in direct communication with the outlet end to a second position which places the inlet end in communication with the diversion branch;
(b) a housing connected to the diversion branch of said flow diverting valve and having a downwardly opening bore formed therein;
(c) a specimen container demountably connected to the open bore of said housing; and
(d) an overflow pipe connected between said housing and the outlet end of said flow diverting valve.

* * * * *